United States Patent
Berriman

(10) Patent No.: US 9,849,219 B2
(45) Date of Patent: Dec. 26, 2017

(54) METHODS FOR HARVESTING HUMAN FIBROBLASTS, AND AUTOGRAFTING METHODS

(71) Applicant: DermaGenesis, Miami, FL (US)

(72) Inventor: Sandra Berriman, Boca Raton, FL (US)

(73) Assignee: DERMAGENESIS, LLC, Pompano Beach, FL (US)

(*) Notice: Subject to any disclaimer, the term of this patent is extended or adjusted under 35 U.S.C. 154(b) by 319 days.

(21) Appl. No.: 14/656,842

(22) Filed: Mar. 13, 2015

(65) Prior Publication Data

US 2015/0258246 A1    Sep. 17, 2015

Related U.S. Application Data

(60) Provisional application No. 61/953,362, filed on Mar. 14, 2014.

(51) Int. Cl.

| | | |
|---|---|---|
| *A61L 27/60* | (2006.01) | |
| *A61L 27/36* | (2006.01) | |
| *A61L 27/38* | (2006.01) | |
| *A61B 17/322* | (2006.01) | |
| *A61B 17/00* | (2006.01) | |

(52) U.S. Cl.
CPC ............ *A61L 27/60* (2013.01); *A61B 17/322* (2013.01); *A61L 27/362* (2013.01); *A61L 27/3804* (2013.01); *A61B 2017/00969* (2013.01); *A61B 2017/3225* (2013.01); *A61L 2430/40* (2013.01)

(58) Field of Classification Search
CPC .... A61L 27/60; A61L 27/362; A61L 27/3813; A61B 2017/00969; A61B 2017/3225
See application file for complete search history.

(56) References Cited

U.S. PATENT DOCUMENTS

| | | | | |
|---|---|---|---|---|
| 2011/0318414 A1* | 12/2011 | Jackson | .................... | A61F 2/02 424/484 |
| 2012/0265228 A1* | 10/2012 | Peterson | ........ | A61B 17/320708 606/170 |
| 2015/0174291 A1* | 6/2015 | Zimnitsky | ........... | A61L 26/0038 604/290 |

OTHER PUBLICATIONS

You et al., "Three types of dermal grafts in rats: the importance of mechanical property and structural design", Biomedical Engineering Online, 2013, vol. 12, No. 125.
Tuan et al., "Dermal fibroblasts activate keratinocyte outgrowth on collagen gels", Journal of Cell Science, 1994, pp. 2285-2289, vol. 107.
Wang et al., "Enhanced Keratinocyte Proliferation and Migration in Co-culture with Fibroblasts", Plos One, Jul. 2012, e40951, vol. 7, No. 7.
Potter et al., "An Investigation to Optimize Angiogenesis within Potential Dermal Replacements", Plastic and Reconstructive Surgery, May 2006, pp. 1876-1885, vol. 117, No. 6.
Werner et al., "Keratinocyte-Fibroblast Interactions in Wound Healing", Journal of Investigative Dermatology, 2007, pp. 998-1008, vol. 127.

(Continued)

*Primary Examiner* — Katrina Stransky
*Assistant Examiner* — Daniel Bissing
(74) *Attorney, Agent, or Firm* — Whitham, Curtis & Cook

(57) ABSTRACT

Autografts are produced using material harvested from the patient without creation of a new wound. For example, material is harvested from the patient's very wound to which the autograft is to be applied.

2 Claims, 2 Drawing Sheets

(56) References Cited

OTHER PUBLICATIONS

Metcalfe et al., "Tissue engineering of replacement skin: the crossroads of biomaterials, wound healing, embryonic development, stem cells and regeneration", J. R. Soc. Interface, 2007, pp. 413-437, vol. 4.

Rodriguez-Menocal et al., "Stimulation of Skin and Wound Fibroblast Migration by Mesenchymal Stem Cells Derived from Normal Donors and Chronic Wound Patients", Stem Cells Translational Medicine, 2012, pp. 221-229, vol. 1.

\* cited by examiner

METHODS FOR HARVESTING HUMAN FIBROBLASTS, AND AUTOGRAFTING METHODS

FIELD OF THE INVENTION

The invention relates to the medical arts, more particularly, to tissue engineering especially tissue engineering in which three-dimensional printing technology is used.

BACKGROUND OF THE INVENTION

Healing wounds is a complex process of tissue repair and regeneration in response to injury. The healing response in skin wounds (Inflammation, proliferation and repair, and tissue remodeling) attempts to reconstitute tissue similar to the wounded one and this is accomplished via the concerted action of numerous skin cell types, collagens, cytokines, growth factors (GF s), chemokines, cell surface and adhesion molecules, as well as multiple extracellular matrix proteins. Skin grafting becomes necessary in many wounds to prevent massive water loss in addition to providing protection against infection during the healing process. Autologous split-thickness skin grafting currently represents the most rapid, effective method of reconstructing large skin defects; however, in cases where a significant quantity of harvested graft is required, it represents yet another trauma to an already injured patient.

Much auto-grafting work has been done previously including our own work and that of others.

Previously, we have described production of a customized skin graft that is preferably accomplished by operation of a three-dimensional printer that is supplied with substrate material and autologous skin cells. The printer then "prints" the supplied skin cells in a particular order, pattern, or by cell type to execute the fabrication of the skin graft. The major objective of the production of a skin graft via 3-Dimensional printing technology is to use the patient's own skin cells to re-create a strong, persistent, organ replacement solution.

The most important and abundant cell type for the development of the autologous skin graft is fibroblast cells. Fibroblasts comprise the bulk of the cells that form and remodel the extracellular matrix and thus, harvesting large numbers for further proliferation and use in the formation of the autologous graft, is essential.

Fibroblasts synthesize substances, including collagen, that form and rearrange the extracellular matrix. They play a crucial role in wound healing and can behave like stem cells capable of phenotypic alteration most commonly to keratinocytes, the primary skin cell type of the epidermal layer. Other fibroblasts are focused on maintenance and tissue metabolism.

In the previous auto-grafting work, as the source of fibroblasts to be autografted onto the patient's wound, standard practice has been to harvest from a donor site selected by the medical practitioner from unwounded dermal tissue elsewhere on the patient, thereby creating a new, additional wound at the donor site in addition to the original wound onto which an autograft is to be placed.

SUMMARY OF THE INVENTION

The present invention provides an autografting method without necessarily creating a new secondary wound. Surprisingly, the very wound to which the autograft is to be applied is used as the source of material processed into an autograft.

In a preferred embodiment, the invention provides a method of autografting a wound (such as, e.g., a chronic wound; diabetic foot ulcers; other diabetic wounds; burn wounds; venous leg ulcers; other venous ulcers; pressure ulcers; other chronic wounds; acute wounds; surgical wounds; trauma wounds; etc.) on a patient, comprising harvesting (such as, e.g., harvesting comprising performing surgical debridement) a quantity of tissue (such as, e.g., granulation tissue) from the wound, processing the harvested tissue (such as, e.g., harvested tissue that comprises one or more selected from the group consisting of: fibroblasts; collagen; cells from the patient's immune system; endothelial cells) into an autograft, and applying the autograft to the wound from which the quantity of tissue was harvested, such as, e.g., inventive methods wherein the patient has been autografted without creation of a new donor site wound; inventive methods that comprise performing surgical debridement to obtain fresh granulation tissue; inventive methods that comprise obtaining the granulation tissue from the wound using surgical dissection; inventive methods that comprise obtaining the granulation tissue from the wound by debridement; inventive methods in which tissue is harvested from inside the wound margins (i.e., edges) of the wound bed; inventive methods that comprise scraping the wound bed (such as, e.g., scraping the wound bed and during scraping, avoiding the keratinocyte layer and necrotic tissue); inventive methods further comprising applying negative pressure to the wound before and/or during harvesting tissue from the wound; inventive methods further comprising a step of initiating granulation tissue formation by performing surgical debridement of the wound, performed before the step of harvesting tissue from the wound (such as, e.g., an initiating step performed about 0-3 days before the harvesting step); and other inventive methods.

The invention in another preferred embodiment provides a method of harvesting tissue of a patient to be used in an autograft on the patient, consisting of harvesting only from an existing wound on the patient, such as, e.g., inventive methods performed without creating a new donor-site wound; and other inventive methods.

In another preferred embodiment, the invention provides a method of producing an autograft to be applied to a preexisting wound (such as, e.g., a chronic wound; diabetic foot ulcers; other diabetic wounds; burn wounds; venous leg ulcers; other venous ulcers; pressure ulcers; other chronic wounds; acute wounds; surgical wounds; trauma wounds; etc.) of a patient, consisting of the steps of: harvesting material from the preexisting wound; and processing the harvested material into an autograftable form useable as the autograft, wherein the autograft has been produced without creation of a new donor site wound to the patient.

DETAILED DESCRIPTION OF THE INVENTION

Figure 2:
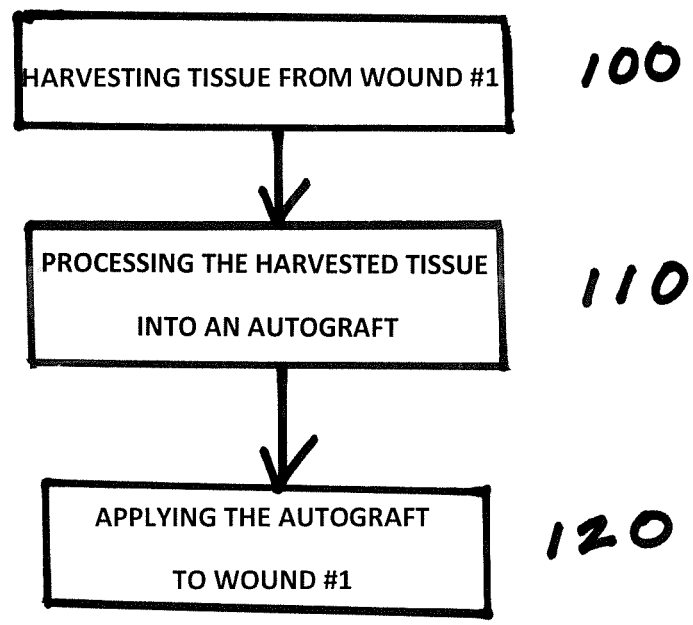
FIG. 2 is a flow chart of an exemplary embodiment of an inventive method.

Referring to FIG. 2, inventive steps are performed of harvesting 100 tissue from a wound, followed by processing 110 the harvested tissue into an autograft, followed by applying 120 the autograft to the same wound used in the harvesting step.

That the wound in the harvesting 100 and autograft-applying 120 steps is the same wound is particularly emphasized.

With regard to the patient's dermis elsewhere than wound #1 being used in the harvesting 100 and autograft-applying 120 steps, in some embodiments the patient is spared creation of a new donor site wound otherwise than wound #1, and in other embodiments creation of a new donor site wound otherwise than wound #1 optionally is performed.

Most preferably, the method steps of FIG. 2 preferably are performed without creating a new secondary wound ("new donor site wound"). Herein when we refer to a "donor site wound", we refer to a substantial dermal wound created by a surgeon or medical personnel who consider the new dermal wound medically necessary in order to obtain biological material to be donated by the patient towards autograft preparation. A pinprick incision or a needle insertion, as examples, are not considered a "donor site wound". Examples of creating a "donor site wound" are, e.g., surgically creating a donor site wound; creating a donor site wound by separating tissue using a laser; raising a blister and separating the blister.

Preferably the harvested tissue comprises granulation tissue. Granulation tissue comprises mostly fibroblasts and also comprises tissue matrix which comprises collagen; cells from the patient's immune system; and endothelial cells. As the granulation tissue harvested and used in the invention, granulation tissue that is fresh (i.e., granulation tissue at about days 1-3 following surgical (sharp) debridement of the wound) is preferred.

As to quantity of tissue harvested from the existing patient wound in the harvesting step, the quantity is a function of certain characteristics of the wound, such as wound size and wound position. A sufficient quantity of harvested cells is wanted; if too small a quantity is harvested, recovery and adequate expansion of cells could be affected. An overlarge quantity of harvested cells is not preferred; when an excessive quantity is harvested, the integrity of the cells could be affected by storage, transport, nutrient deficits, or further isolation techniques. In a case of a diabetic foot wound of a diameter averaging 3-5 cm, preferably a quantity of tissue of at least 0.5 g is harvested; more preferably a quantity of tissue of at least 1.5 g is harvested; in the harvesting step preferably a quantity of tissue of no more than 20.0 g is harvested from the existing patient wound. In a case of a wound on an abdomen of a diameter averaging 10 cm, preferably a quantity of tissue of at least 0.5 g is harvested; more preferably a quantity of at least 1.5 g is harvested; in the harvesting step preferably a quantity of tissue of no more than 20.0 g is harvested from the existing patient wound.

In the tissue-harvesting step, preferably tissue is obtained from a dermal layer of the wound bed section of the existing patient wound. Preferably the keratinocyte layer of the existing patient wound is avoided and NOT harvested. Preferably necrotic tissue is avoided and NOT harvested.

Most preferably, the wound from which the harvesting is performed does not, at the time of the harvesting step, extend down to bone. Most wounds that extend down to bone would not be feasible to use in the harvesting step of the invention.

Optionally before harvesting step 100 is performed, negative pressure is applied, such as, e.g., application of negative pressure for up to 3 days following initial wounding.

The invention may be further appreciated with reference to the following examples, without the invention being limited thereto.

EXAMPLE 1

This inventive Example is of a method for harvesting fibroblasts capable of replicating at high rates thus providing substantial material for constructing autologous skin grafts for wound healing. Instead of harvesting skin donor sites and dissociating fibroblasts from the dermal cell layers, the patient's own wound is used as the tissue donor site. During the proliferation phase of wound healing, the wound bed forms granulation tissue. Granulation tissue fills in the wound bed as it heals and is composed of supporting cells of all types including fibroblasts which form and remodel the extracellular matrix to maintain structural integrity; neutrofils, macrophages and other components of the immune system response; and endothelial cells and growth factors that support angiogenesis. The present inventor has observed that fibroblasts, when isolated from wound granulation tissue, proliferate in culture at a much faster rate than do fibroblasts harvested from full thickness skin biopsies.

Harvesting fibroblasts from granulation tissue is believed to deliver a fibroblast in a more "activated" state.

Method for Harvesting Granulation Tissue and Isolating Fibroblasts:

A sample of granulation tissue is obtained from the patient's wound bed using surgical dissection or standard debridement techniques. Surgical debridement is done using scalpels, forceps, scissors, and other sharp instruments. This sample is placed into small conical tubes in phosphate buffered saline (PBS) with 4% penicillin/streptomycin/fungizone (P/S/F). The sample is held in this solution for further processing (~5 hrs). At times it is necessary for samples to be held overnight at 4° C. when patient tissue samples are shipped to laboratory. Once back in the lab, the sample is blotted dry to remove excess liquid and weighed (2.78 g). The sample is washed 3× in PBS-P/S/F then chopped into small (2-4 mm$^3$ pieces) and immersed in 25 mL of collagenase A (0.5 mg/mL) or other widely accepted enzymes. This tissue is incubated at 37° C. overnight and agitated to facilitate tissue digestion. The digestion mixture is then centrifuged for 10 min at 1200 rpm, pellet resuspended and passed over a 70 µm filter to remove any fibrous cell debris. The isolated cells are washed with culture medium and recentrifuged as above—this is repeated 3×. Cells are reconstituted in 5 mL DMEM and counted using a hemocytometer.

EXAMPLE 1A

Figure 1:
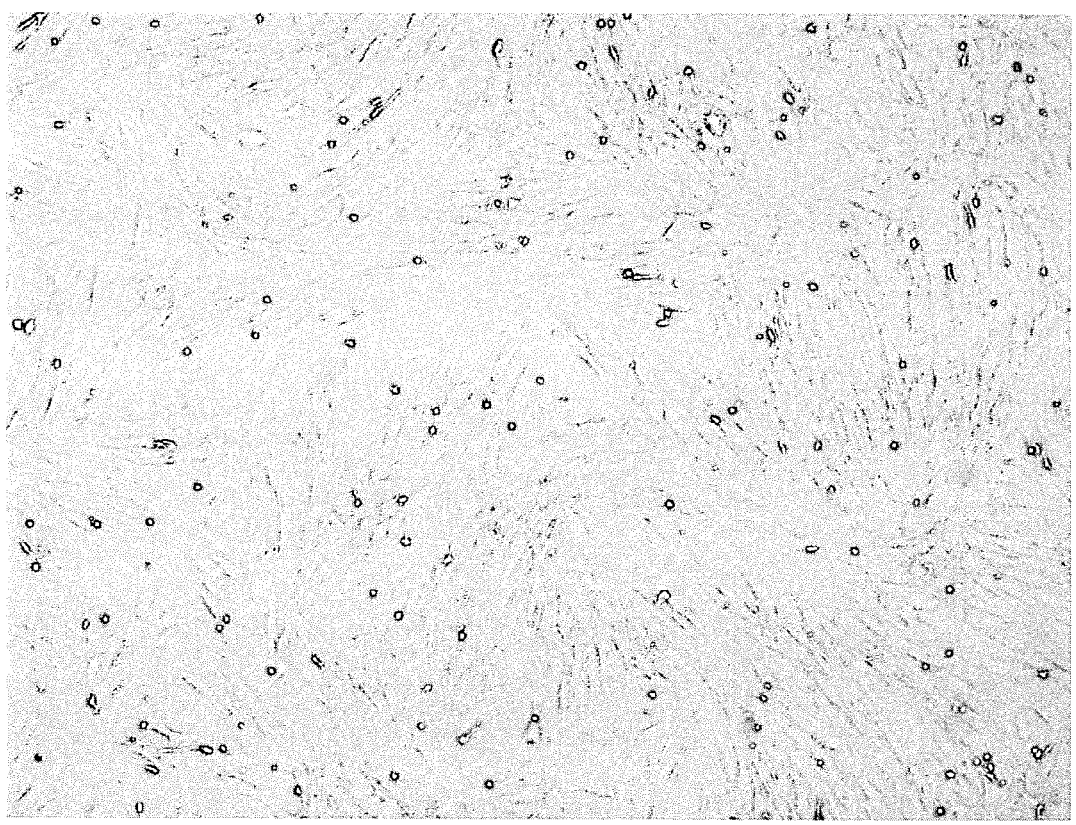
FIG. 1 is an image taken of fibroblasts isolated from granulation tissue in an exemplary embodiment of the invention.

The procedures of Example 1 were followed and an image (FIG. 1) was taken of fibroblasts isolated from granulation tissue. Cell counts (FIG. 1) that were observed would suggest a 9 to 25-fold expansion over 24 hours compared to fibroblasts isolated from the same size sample of a full thickness skin graft.

A major advantage of harvesting fibroblasts from wound granulation tissue is that skin donor sites will no longer be necessary which obviates the need to injure the patient further.

While the invention has been described in terms of a preferred embodiment, those skilled in the art will recognize that the invention can be practiced with modification within the spirit and scope of the appended claims.

REFERENCES

1) T-L Tuan, et al. Dermal fibroblasts activate keratinocytes outgrowth on collagen gels. 1994; 107:2285-2289.
2) A D Metcalfe, M W J Ferguson. Tissue engineering of replacement skin: the crossroads of biomaterials, wound healing, embryonic development, stem cells and regeneration. J.R. Soc. Interface (2007) 4, 413-437.
3) S Werner, et al. Keratinocyte-Fibroblast interactions in wound healing. J Investig. Derm (2007) 127, 998-1008.
4) K J Potter, et al. An Investigation to Optimize Angiogenesis within Potential Dermal Replacements. Plast. Reconstru. Surg. (2006), 117, 1876-1885.
5) L Rodriguez-Menocal, et al. Stimulation of Skin and Wound Fibroblast Migration by Mesenchymal Stem Cells Derived from Normal Donors and Chronic Wound Patients. Stem Cells Translation Med (2012); 1, 221-229.
6) C You, et al. Three types of Derm Graft in Rats: the Important of Mechanical Property and Structural Design. BioMedical Engineering OnLine (2013), 12:1-17.
7) Z Wang, et al. Enhanced Keratinocyte Proliferation and Migration in Co-Culture with Fibroblasts. PLoS one (2012) 7, 1-12.

What I claim as my invention is:

1. A method of autografting a wound on a patient, comprising:

harvesting a quantity of tissue from the wound, wherein in the harvesting step, the quantity of tissue harvested is in a range of 0.5 g to 20.0 g from a diabetic foot wound;

processing the harvested tissue into an autograft, and applying the autograft to the wound from which the quantity of tissue was harvested.

2. A method of autografting a wound on a patient, comprising:

harvesting a quantity of tissue from the wound, wherein the harvesting step comprises scraping the wound bed, further comprising, during scraping, avoiding the keratinocyte layer and necrotic tissue;

processing the harvested tissue into an autograft, and applying the autograft to the wound from which the quantity of tissue was harvested.

* * * * *